United States Patent [19]
Lantzsch et al.

[11] Patent Number: 5,824,817
[45] Date of Patent: Oct. 20, 1998

[54] HERBICIDAL COMPOSITIONS BASED ON 2,6-DICHLORO-3-FLUORO-BENZONITRILE, AND NEW INTERMEDIATES

[75] Inventors: Reinhard Lantzsch, Wuppertal; Werner Bussmann, Leverkusen; Josef Käsbauer, Wermelskirchen; Markus Dollinger; Hans-Joachim Santel, both of Leverkusen, all of Germany

[73] Assignee: Bayer Aktiengesellschaft, Leverkusen, Germany

[21] Appl. No.: 901,296

[22] Filed: Jul. 28, 1997

Related U.S. Application Data

[62] Division of Ser. No. 559,750, Nov. 15, 1995, abandoned.

[30] Foreign Application Priority Data

Nov. 22, 1994 [DE] Germany ............... 4441419.6

[51] Int. Cl.$^6$ .................... C07C 255/33; C07C 47/54
[52] U.S. Cl. .................... 558/425; 564/182; 564/265; 568/312; 568/343; 568/348; 568/425
[58] Field of Search .................... 564/182, 265; 568/312, 343, 348, 425; 558/425

[56] References Cited

U.S. PATENT DOCUMENTS 5,475,164  12/1995  Bussmann ............... 570/144

FOREIGN PATENT DOCUMENTS

| 0273317 | 7/1988 | European Pat. Off. . |
| 0599241 | 6/1994 | European Pat. Off. . |
| 0609179 | 8/1994 | European Pat. Off. . |
| 0657407 | 6/1995 | European Pat. Off. . |
| 1232614 | 10/1960 | France . |

OTHER PUBLICATIONS

Chemical Abstracts, vol. 115, No. 17, Oct. 28, 1991, 1–Pharmacology, C. Paul Bianchi, pp. 1, 878–879.

Primary Examiner—Johann Richter
Assistant Examiner—Ebenezer O. Sackey
Attorney, Agent, or Firm—Sprung Kramer Schaefer & Briscoe

[57] ABSTRACT

The invention relates to the use of the known compound 2,6-dichloro-3-fluoro-benzonitrile as active compound in selectively-herbicidal compositions, and to new preparation processes and new intermediates for the preparation of this compound.

5 Claims, No Drawings

HERBICIDAL COMPOSITIONS BASED ON 2, 6-DICHLORO-3-FLUORO-BENZONITRILE, AND NEW INTERMEDIATES

This application is a divisional of application Ser. No. 08/559,750, filed Nov. 15, 1995 now abandoned.

The invention relates to the use of the known compound 2,6-dichloro-3-fluoro-benzonitrile as active compound in selectively herbicidal compositions and to new preparation processes and new intermediates for the preparation of this compound.

2,6-Dichloro-3-fluoro-benzonitrile has already been disclosed as an intermediate for the preparation of 2,3,6-trifluoro-benzonitrile (cf. JP-A 03090057—cited in Chem. Abstracts 115:182866). However, the use of the abovementioned compound as a herbicide has not been disclosed to date. With regard to the preparation, the literature cited mentions that 3-chloro-2,4-difluoro-nitrobenzene is first reacted with an alkali metal cyanide, giving 2-chloro-3-fluoro-6-nitro-benzonitrile, which is then converted by reacting it with chlorine to give 2,6-dichloro-3-fluoro-benzonitrile. Yield and quality of the product thus obtained are not always entirely satisfactory.

It has now been found that the compound 2,6-dichloro-3-fluoro-benzonitrile, of the formula (I) below

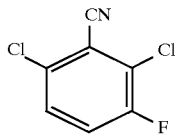
(I)

is highly suitable for selectively combating weeds in important cultures.

Furthermore, it has been found that the compound of the formula (I) is obtained when 2,6-dichloro-3-fluoro-benzaldoxime, of the formula (II), or 2,6-dichloro-3-fluoro-benzamide, of the formula (III),

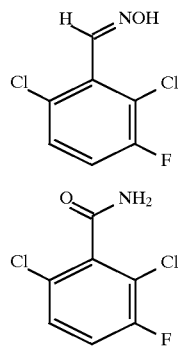
(II)

(III)

is reacted with a dehydrating agent at temperatures between 0° C. and 300° C. in a pressure range of between 0.001 bar and 10 bar (cf. the preparation examples).

Surprisingly, the compound of the formula (I) to be used according to the invention can be prepared by the preparation process according to the invention considerably more simply and in very high yields, using readily accessible starting materials.

The starting materials of the formulae (II) and (III) were hitherto unknown from the literature; they are new substances and provided by the present application.

The new compound of the formula (II) is obtained when 2,6-dichloro-3-fluoro-benzaldehyde, of the formula (IV),

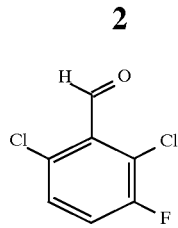
(IV)

is reacted with hydroxylamine or an acid adduct thereof, such as, for example, hydroxylamine hydrochloride, at temperatures between 0° C. and 100° C., if appropriate in the presence of a diluent, such as, for example methanol, ethanol and/or water, and, if appropriate, in the presence of an acid acceptor, such as, for example, sodium acetate (cf. the preparation examples).

The new compound of the formula (III) is obtained when 2,6-dichloro-3-fluorobenzoic acid, of the formula (V),

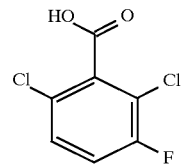
(V)

is reacted with a chlorinating agent, such as, for example, thionyl chloride, at temperatures between 0° C. and 100° C., if appropriate in the presence of a reaction auxiliary, such as, for example, N,N-dimethyl-formamide, and the resulting 2,6-dichloro-3-fluorobenzoyl chloride is reacted with ammonia at temperatures between −50° C. and +50° C., if appropriate in the presence of a diluent, such as, for example, water (cf. the preparation examples).

2,6-Dichloro-3-fluoro-benzaldehyde, of the formula (IV), which is to be used as a precursor, if appropriate, was hitherto unknown from the literature and a new substance also provided by the present application.

The new compound of the formula (IV) is obtained when 2,6-dichloro-3-fluorobenzal chloride, of the formula (VI),

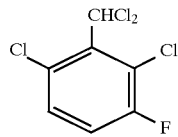
(VI)

is reacted with water at temperatures between 0° C. and 200° C., if appropriate in the presence of a reaction auxiliary, such as, for example, hydrogen chloride and/or iron(III) chloride (cf. the preparation examples).

2,6-Dichloro-3-fluoro-benzal chloride, of the formula (VI), which is required for this purpose as a precursor was hitherto unknown from the literature and a new substance also provided by the present application.

The new compound of the formula (VI) was obtained when 2,6-dichloro-3-fluorotoluene, of the formula (VII),

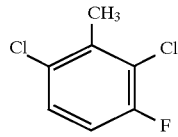
(VII)

is reacted with chlorine at temperatures between 0° C. and 100° C., if appropriate in the presence of a reaction auxiliary, such as, for example, pyridine (cf. the preparation examples).

2,6-Dichloro-3-fluoro-toluene, of the formula (VII), was hitherto not known from the literature but is a new substance provided by an earlier patent application.

The compound of the formula (VII) is obtained by reacting 3-fluoro-toluene, of the formula (VIII),

with chlorine at temperatures between 0° C. and 100° C., if appropriate in the presence of a reaction auxiliary, such as, for example iron(III) chloride and 2,3-dihydro-5H-benzo[b]-1,4-thiazepin-4-one (cf. the preparation examples).

3-Fluoro-toluene is a conmmercially available chemical for synthesis.

2,6-Dichloro-3-fluoro-benzoic acid, of the formula (V), which is to be used as a precursor, if appropriate, was hitherto unknown from the literature and is a new substance provided by the present application.

The new compound of the formula (V) is obtained when 2,6-dichloro-3-fluorobenzaldehyde, of the formula (IV)— above—, is reacted with an oxidant, such as, for example, hydrogen peroxide, at temperatures between 0° C. and 100° C., if appropriate in the presence of a reaction auxiliary, such as, for example, sodium hydroxide, and, if appropriate, in the presence of a diluent, such as, for example, water (cf. the preparation examples).

The process according to the invention for the preparation of the compound of the formula (I) is carried out using a dehydrating agent. Suitable dehydrating agents are the customary agents which are suitable for dehydrating aldoximes. Examples which may be mentioned are acetic anhydride, thionyl chloride, phosphorus(V) oxide, dicyclohexylcarbodiimide, cyanuric chloride, titanium(IV) chloride and benzenesulphonyl chloride.

When carrying out the process according to the invention for the preparation of the compound of the formula (I), the reaction temperatures can be varied within a substantial range. In general, the process is carried out at temperatures between 0° C. and 300° C., preferably at temperatures between 20° C. and 250° C., in particular temperatures between 50° C. and 200° C.

The process according to the invention for the preparation of the compound of the formula (I) is generally carried out under atmospheric pressure. However, it is also possible to carry out the process under elevated or reduced pressure—in general between 0.001 bar and 10 bar, preferably between 0.01 bar and 5 bar, in particular between 0.1 bar and 2 bar.

To carry out the process according to the invention for the preparation of the compound of the formula (I), at least one 1 mol of a dehydrating agent is generally employed per mole of starting compound of the formula (II) or of the formula (III). The dehydrating agent can also be employed in a large excess and therefore also act as the diluent, preferably when acetic anhydride is employed. Reaction and work-up are carried out by customary methods (cf. the preparation examples).

The active compound to be used in accordance with the invention can be used as a defoliant, desiccant, agent for destroying broad-leaved plants and, especially, as a weed-killer. By weeds, in the broadest sense, there are to be understood all plants which grow in locations where they are undesired. Whether the substance according to the invention acts as a total or selective herbicide depends essentially on the amount used.

The active compound to be used in accordance with the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera; Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compound according to the invention is in no way restricted to these genera, but also extends in the same manner to other plants.

The active compound of the formula (I) is suitable, depending on the concentration, for the total combating of weeds, for example on industrial terrain and rail tracks, and on paths and squares with or without tree plantings. Equally, the compound can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasturage, and for the selective combating of weeds in annual cultures.

The compound of the formula (I) to be used in accordance with the invention is particularly suitable for selectively combating monocotyledon and dicotyledon weeds in monocotyledon and dicotyledon cultures by the pre- as well as the post-emergence methods.

The active compound can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compound with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifing and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

For combating weeds, the active compound to be used in accordance with the invention, as such or in the form of its formulations, can also be used as a mixture with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compound can be used as such, in the form of its formulations or in the use forms prepared therefrom by further dilution, such as ready-to-use solutions, suspensions, emulsions, powders, pastes and granules. They are used in the customary manner, for example by watering, spraying, atomizing or scattering.

The active compound to be used in accordance with the invention can be applied either before or after emergence of the plants. It can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compound according to the invention can be seen from the following examples.

PREPARATION EXAMPLES

Example 1

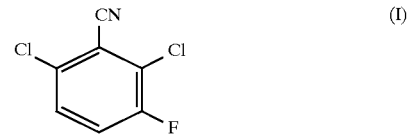

(I)

80 g (0.385 mol) of 2,6-dichloro-3-fluoro-benzaldoxime, of the formula (II), are mixed with 500 ml of acetic anhydride at room temperature (approximately 20° C.). This gives a clear solution which is then stirred at 135° C. for 6 hours. After acetic acid and acetic anhydride have been distilled off, the residue is cooled to room temperature and taken up in methylene chloride. The solution is washed three times with water and then dried using sodium sulphate and filtered. The solvent is then carefully removed from the filtrate by distillation under reduced pressure.

67 g (91% of theory) of 2,6-dichloro-3-fluoro-benzonitrile are obtained as a crystalline residue of melting point 69° C.–71° C.

Example 2

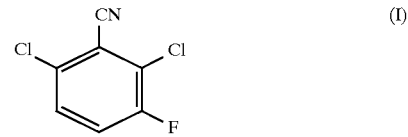

(I)

In a small distillation apparatus, a mixture of 2.08 g (0.01 mol) of 2,6-dichloro-3-fluoro-benzamide and 1.6 g (0.011 mol) of phosphorus(V) oxide is heated at approximately 200° C. at a pressure of approximately 100 bar.

This gives 1.4 g (74% of theory) of 2,6-dichloro-3-fluoro-benzonitrile of melting point 70° C.–72° C.

Starting Compound of the Formula (II)

Example (II-1)

78.3 g (0.383 mol) of 2,6-dichloro-3-fluoro-benzaldehyde (94.5% pure)—dissolved in 150 ml of methanol—are added dropwise to a solution of 31 g (0.446 mol) of hydroxylamine hydrochloride and 36.6 g (0.446 mol) of sodium acetate in 400 ml of methanol and 40 ml of water. The reaction is exothermc (32° C.). Stirring is continued at room temperature (20° C.) for twelve hours and the mixture is filtered. The solid is extracted twice by stirring with water and filtered off. Melting point: 130° C.–131° C. More reaction product can be obtained by concentrating the mother liquor and precipitation with water.

Total yield: 80 g (product purity 94.8%); yield: 94% of theory.

Starting Compound of the Formula (III)

Example (III-1)

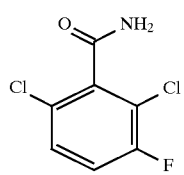

20.9 g (0.1 mol) of 2,6-dichloro-3-fluoro-benzoic acid, 100 ml of thionyl chloride and a few drops of dimethylformamide are heated at the boil for 3 hours. The residue which remains after the excess thionyl chloride has been distilled off is added dropwise to 300 ml of concentrated ammonia solution. The solids are filtered off, washed with water and dried.

Yield: 20.4 g (98% of theory) of 2,6-dichloro-3-fluoro-benzamide of melting point 183° C.–186° C.

Starting Compounds of the Formula (IV)

Example (IV-1)

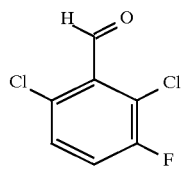

200 g (0.85 mol) of 2,6-dichloro-3-fluoro-benzal chloride are introduced into a four-necked flask equipped with stirrer, reflux condenser, thermometer and dropping funnel. 200 mg of iron(III) chloride—dissolved in 23 ml of hydrochloric acid (32% strength)—are then added dropwise at 160° C. in the course of 4 hours. This gives a crude aldehyde containing less than 0.7% of the benzal chloride.

After distillation in vacuo (20 mbar), 120 g of pure 2,6-dichloro-3-fluorobenzaldehyde (98.5% pure) are obtained, yield: 77% of theory.

Starting Compound of the Formula (V)

Example (V-1)

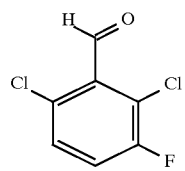

11.6 g (0.06 mol) of 2,6-dichloro-3-fluoro-benzaldehyde (94.5% pure) is molten in 30 ml of water at 60° C., and 1 ml of 30% strength sodium hydroxide solution is added with vigorous stirring.

29.1 g (0.3 mol) of hydrogen peroxide (35% strength) and 12 g (0.09 mol) of sodium hydroxide solution (30% strength) are subsequently metered in simultaneously from two dropping funnels. During this process, this reaction temperature climbs to 70° C. The mixture is held at this temperature for a further hour, and the clear reaction solution is then allowed to cool. The mixture is extracted twice using methylene chloride and the pH is brought to 1. The solids are filtered off, washed with water and dried. Yield: 10.5 g (83% of theory); melting point: 127° C.–131° C.

Starting Compound of the Formula (VI)

Example (VI-1)

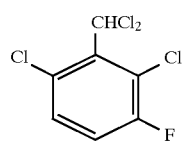

360 g of a mixture of dichlorofluorotoluene isomers (50% of 2,6-dichloro-3-fluoro-toluene) are introduced into a reaction vessel. After 1 drop of pyridine has been added, chlorine is introduced until the 2,6-isomer has been converted completely to 2,6-dichloro-3-fluoro-benzal chloride. The approximate composition of the resulting mixture is 45% of 2,6-dichloro-3-fluoro-benzal chloride, 45% of 4,6-dichloro-3-fluoro-benzal chloride and 5% of 4,6-dichloro-3-fluoro-benzotrichloride.

This mixture is separated by fractional distillation. The result is a main fraction containing 98.5% of 2,6-dichloro-3-fluoro-benzal chloride, which is used directly in the hydrolysis reaction; yield: 200 g (80% of theory).

Starting Compound of the Formula (VII)

Example (VII-1)

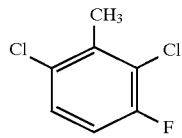

330 g of 3-fluoro-toluene are introduced into a four-necked flask equipped with stirrer, reflux condenser, thermometer and gas inlet tube. After 2.3 g of iron(III) chloride and 450 mg of 2,3-dihydro-5H-benzo[b]-1,4-thiazepin-4-one have been added, chlorine is passed in with stirring at 20° C., until only 1 percent by weight of the monochloro derivative remains. A mixture comprising 43% of 4,6-dichloro-3-fluoro-toluene and 43 percent by weight of 2,6-dichloro-3-fluoro-toluene is obtained.

The reaction mixture is washed twice with water (in each case 60 ml) and subsequently distilled. This gives first runnings (60 g) which comprise essentially monochlorofluorotoluene and are added to the next batch. 360 g of the isomer mixture are obtained as the main fraction, and the residue which remains is again reused.

After this has been repeated five times, the yield is 80% of theory.

The isomer mixture obtained, which comprises 50% of 2,6- and 50% of 4,6-dichloro-3-fluoro-toluene, is used directly in the next step.

Use Examples

Example A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. After three weeks, the degree of damage to the plants is rated in % damage in comparison with the development of the untreated control. The figures denote:

0%=no action (like untreated control)

100%=total destruction

In this test, the compound of the formula (I), applied at a rate of 2000 g/ha, shows a very good tolerance by crop plants such as, for example, wheat and soya beans (in each case 10%) and a powerful action against weeds such as Avena (80%) and Galium (80%).

Example B

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, the soil watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison with the development of the untreated control. The figures denote:

0%=no action (like untreated control)

100%=total destruction

In this test, the compound of the formula (I), applied at a rate of 500 g/ha, shows a powerful action against weeds such as Digitaria (100%), Lolium (100%), Panicum (100%), Chenopodium (100%), Galinsoga (100%), Ipomoea (100%) and Stellaria (100%).

It will be understood that the specification and emxamples are illustrative but not limitative of the present invention and that other embodiments within the spirit and scope of the invention will suggest themselves to those skilled in the art.

What is claimed is:

1. A 2,6-dichloro-3-fluoro-phenyl derivative of the formulae

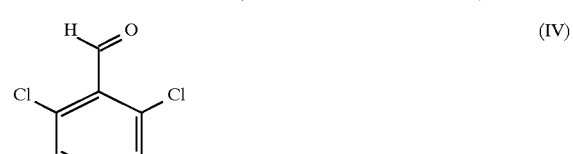

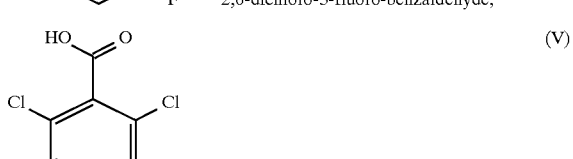

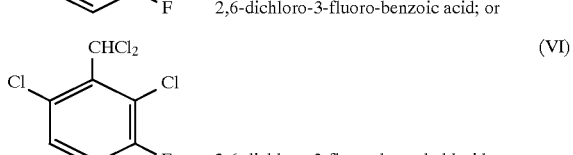

2. Process for the preparation of 2,6-dichloro-3-fluoro-benzaldoxime, according to claim 1 which comprises reacting 2,6-dichloro-3-fluoro-benzaldehyde with hydroxyl amine or an acid adduct thereof at temperatures between 0° C. and 100° C., if appropriate in the presence of a diluent and if appropriate in the presence of an acid acceptor.

3. Process for the preparation of 2,6dichloro-3-fluoro-benzamide, according to claim 1 which comprises reacting 2,6-dichloro-3-fluoro-benzoic acid with a chlorinating agent at temperatures between 0° C. and 100° C., if appropriate in the presence of a reaction auxiliary, and the resulting 2,6-dichloro-3-fluoro-benzoyl chloride is reacted with ammonia at temperatures between −50° C. and +50° C., if appropriate in the presence of a diluent.

4. Process for the preparation of 2,6-dichloro-3-fluoro-benzaldehyde, according to claim 1 which comprises reacting 2,6-dichloro-3-fluoro-benzal chloride with water at temperatures between 0° and 200° C., if appropriate in the presence of a reaction auxiliary.

5. Process for the preparation of 2,6-dichloro-3-fluoro-benzal chloride according to claim 1, which comprises reacting 2,6-dichloro-3-fluoro-toluene with chlorine at temperatures between 0° C. and 100° C., if appropriate in the presence of a reaction auxiliary.

* * * * *